United States Patent

Haber et al.

[11] Patent Number: 5,188,615
[45] Date of Patent: * Feb. 23, 1993

[54] MIXING VIAL

[75] Inventors: Terry M. Haber, Lake Forest; Clark B. Foster, Laguna Niguel; William H. Smedley, Lake Elsinore, all of Calif.

[73] Assignee: Habley Medical Technology Corp., Laguna Hills, Calif.

[*] Notice: The portion of the term of this patent subsequent to May 19, 2009 has been disclaimed.

[21] Appl. No.: 741,780

[22] Filed: Aug. 7, 1991

Related U.S. Application Data

[63] Continuation-in-part of Ser. No. 615,610, Nov. 19, 1990, Pat. No. 5,114,411.

[51] Int. Cl.⁵ .................. A61M 5/24; A61M 37/00
[52] U.S. Cl. ................................. 604/203; 604/87
[58] Field of Search ............. 604/191, 201, 203, 204, 604/239, 411–416, 82, 87–92; 206/221, 222, 218; 220/501, 502, 529, 530, DIG. 34

[56] References Cited

U.S. PATENT DOCUMENTS

| | | | |
|---|---|---|---|
| 2,665,690 | 1/1954 | Lockhart | 206/221 |
| 3,314,563 | 4/1967 | Mounier | 206/221 |
| 3,467,097 | 9/1969 | Ogle | 206/221 |
| 3,521,745 | 7/1970 | Schwartzman | 220/502 |
| 3,779,371 | 12/1973 | Rovinski | 206/221 |
| 4,031,892 | 6/1977 | Hurschman | 206/219 |
| 4,648,532 | 3/1987 | Green | 604/87 |
| 4,779,722 | 10/1988 | Hall | 206/221 |
| 4,886,495 | 12/1989 | Reynolds | |
| 4,927,013 | 5/1990 | Van Brunt et al. | 206/221 |

OTHER PUBLICATIONS

Various photocopies of a cartridge made by Preject.
Various photocopies of a cartridge made by Lyo-Ject.
Mix-O-Vial literature by UpJohn.

Primary Examiner—John D. Yasko
Assistant Examiner—Anthony Gutowski
Attorney, Agent, or Firm—Townsend and Townsend

[57] ABSTRACT

A vial (2, 202) has first and second chambers (56, 232; 54, 234) initially separated by a rupturable barrier (20, 212). The first chamber is a variable volume chamber defined by a cylinder (18, 208), the rupturable barrier at the second end (19, 214) of the cylinder and a piston (14, 228). The second chamber is created by a telescoping container (22, 226) mounted to a second end of the cylinder. The chambers are telescopically collapsed causing fluid pressure in the second chamber to rupture the barrier so the components mix in the first chamber. The piston is driven through the cylinder from pre-mix to post-mix positions by the liquid from the second chamber. This dislodges a safety shield (30, 226) at the first end of the cylidner to expose the piston. The mixed contents of the first, variable volume chamber are removed by inserting a needle cannula through the now exposed piston; aspiration of the mixed contents take place without the introduction of air into the first chamber since the piston moves back down the cylinder as the contents are removed. Structure (236; 242; 248, 250) can be used to prevent the inadvertent activation of the vial (202).

28 Claims, 10 Drawing Sheets

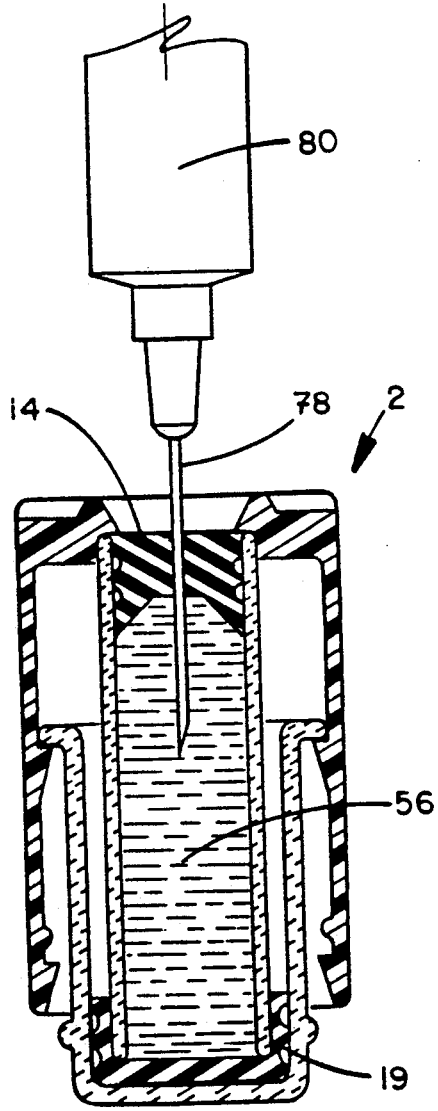
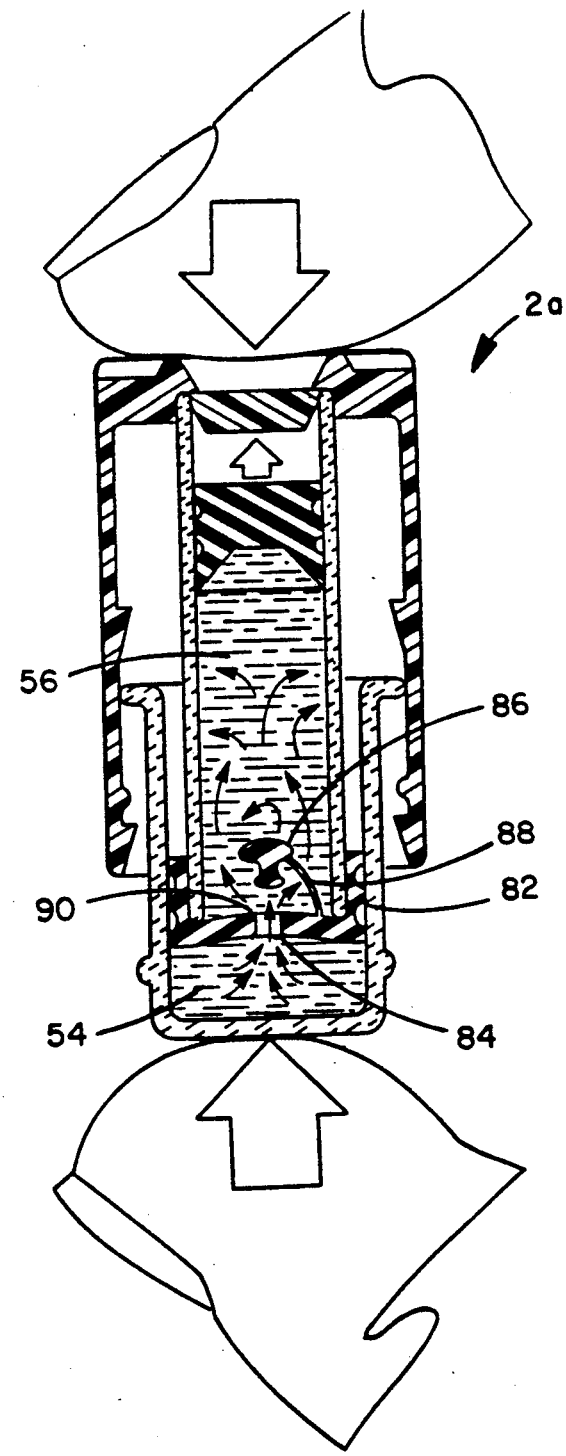
FIG. 6
FIG. 7

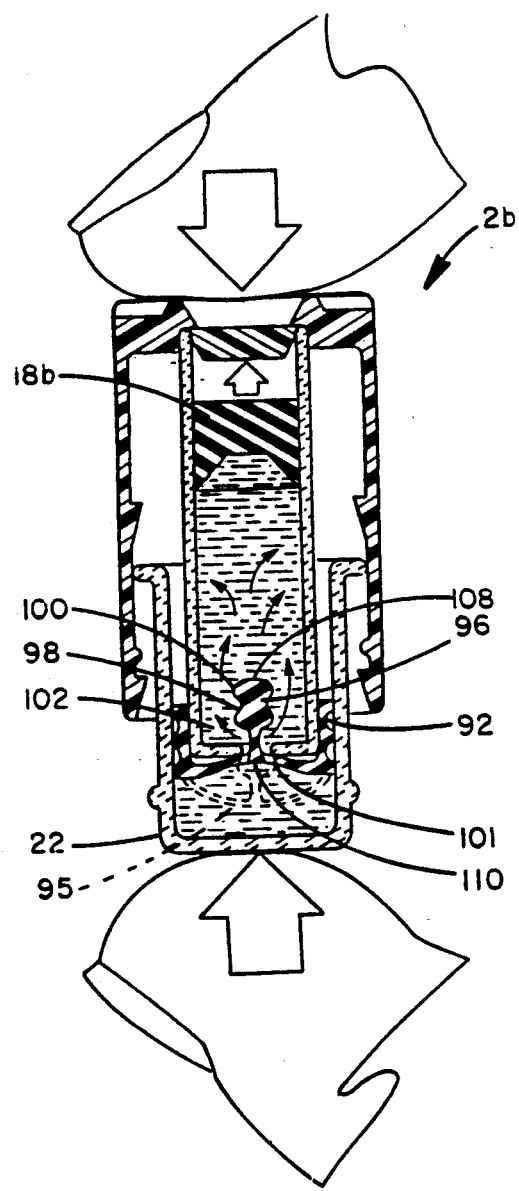
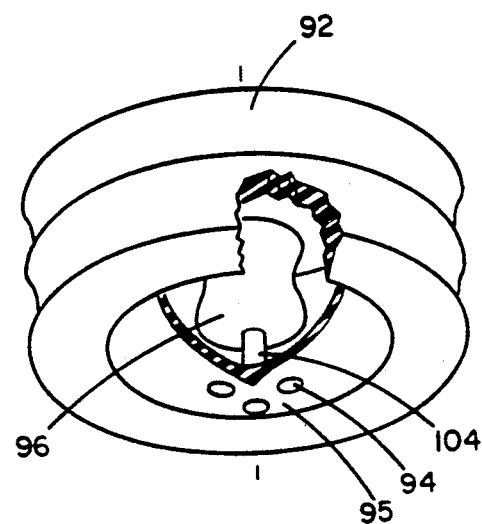
FIG. 8
FIG. 9

MIXING VIAL

This is a Continuation-In-Part of U.S. patent application Ser. No. 07/615,610, filed Nov. 19, 1990 for MULTI-CHAMBER VIAL, (now U.S. Pat. No. 5,114,411) the disclosure of which is incorporated by reference.

BACKGROUND OF THE INVENTION

Safe and effective drug therapy by injection depends not only upon accurate diagnosis, but also on efficient and reliable introduction of the medical substance into the subcutaneous cellular tissue without introducing contaminants or ambient air. The applicable drug or pharmaceutical must first be drawn from the resident container or vial into a syringe before injection. The integrity and features of the vial, therefore, are influential over the overall safety of the injection.

Typically, great care must be taken when a needle cannula of a syringe is used in conjunction with a vial containing a pharmaceutical to be administered to the patient. As the pharmaceutical is drawn out of the container via the needle cannula, precautions must be taken to avoid air being drawn into the syringe. In rigid vials, air must be introduced into the container to fill the void created as the liquid pharmaceutical is withdrawn. This volume of air then becomes susceptible to being mixed with the pharmaceutical or being drawn in through the needle cannula and creating air pockets in the syringe barrel. Catastrophic consequences could result if these air pockets are subsequently injected into the patient along with the liquid pharmaceutical.

Some medical conditions necessitate such a rapid diagnosis and administration of the necessary injection that precautionary measures needed to eliminate air content in the syringe are often compromised. As an example, diagnosis and treatment of acute myocardial infarction requires rapid injection of a thrombolytic agent adjacent to the atherosclerotic plaque in a major epicardial coronary vessel. Minutes, or even seconds, can have profound impact on the treatment of the patient. Thrombolytic agents, such as tissue plasminogen activator (TPA) or streptokinase usually must be injected immediately, while taking the time for necessary precautions needed to prohibit air from becoming entrapped and compromising the drug.

Problems associated with injections are further complicated when the medication to be administered must be stored as two separate component parts, then mixed, prior to injection. Dual chamber vials have been developed to facilitate storage and mixing of these two-component medications. Common examples of multipart medications include medications which must be mixed from a component A, usually a preservative or catalyst, and a component B, which is usually a pharmaceutical. Component A or component B may be in powder or crystalline form instead of liquid form.

Recently, dual chamber vials have been developed which allow an A component and a B component to remain separated in independent chambers within a single package until mixing is desired. The vial allows mixing of the component parts in that same unitary package. In an example of such a device is the MIX-0-VIAL two compartment vial manufactured by the Upjohn Company of Kalamazoo, Mich. This device is a single vial container having two chambers separated by a small stopper. The septum is formed by a plunger-stopper at one end which is used to pressurize the contents of one chamber so to displace a plug lodged in a small orifice separating the two chambers. As the plunger stopper is displaced (by giving it a quarter turn), the plug floats freely into one of the chambers and is used as an agitator to mix the two component parts together. The two components are free to flow between chambers through the connecting orifice and thereby mix together. Although this device is a significant advance in dual chamber vials, the device has least two significant disadvantages. First, once the protective cap is removed, there is nothing to prohibit a user from penetrating the septum with a needle cannula and inadvertently drawing out only one of the component parts separately prior to mixing. Such an event could be extremely hazardous to the health of the patient. Second, even when the two components are properly mixed, when a needle cannula penetrates the septum and draws out the mixed medication, air becomes entrapped in the vial as air enters to replace the removed liquid as the medication is withdrawn. Time consuming precautions must be taken to carefully avoid entrapping air in the syringe and injecting the same into the patient.

SUMMARY OF THE INVENTION

The present invention is directed to a multi-chamber vial which provides both protection against inadvertent withdrawal of one of the component parts of the multipart medication prior to mixing, and a mechanism which eliminates entrapment of air in the medication chamber as the medication is withdrawn.

Generally, the invention relates to vials used for containment of medication substances or pharmaceuticals. More specifically, the invention relates to vial which can store pharmaceuticals made from two component parts where there is a desire to keep the two component parts separated until the time necessary to mix the components together. The device has two (or more) chambers separated by a rupturable barrier which keeps the component parts isolated from each other until mixing is desired. The device is made from materials which eliminate the possibility of a needle cannula accessing either component of the pharmaceutical prior to mixing.

When the components are to be mixed, the contents of one chamber are forced into the other chamber by pressurizing the contents of the one chamber. This is preferably accomplished using a telescoping device so the opposite ends of the device are simply pressed together causing fluid pressure to rupture the barrier separating the two chambers. The one chamber could also be in the form of a flexible bag, a bellows or such other structure. The rupturing can be by dislodging a plug or like element, tearing a flexible diaphragm, breaking a solid frangible sealing element, moving a resilient sealing element, or by other means. Once the barrier is ruptured, the component in the one chamber, termed the second or supplemental chamber, is forced into the other chamber, termed the first or mixing chamber, as the device is compressed. The two components are mixed by the resulting turbulence as the mixing chamber fills with the mixed pharmaceutical.

The mixing chamber is a variable volume chamber. This is achieved by making the mixing chamber a piston and tube, preferably a cylinder, arrangement. The piston travels within the cylinder to increase the size of the mixing chamber as the fluid volume grows. The piston continues to travel until both components are within the mixing chamber; at this point, the piston is forced against a removable safety shield covering the upper end of the cylinder. Only when the safety shield is dislodged from its position covering the end of the cylinder is the user permitted access to the contents of the vial through the piston.

The piston serves several functions: it permits the mixing chamber to be a variable volume chamber to permit mixing of two liquid components without the entrainment of air; it serves as the septum to permit user access to the mixed contents of the mixing chamber by a hollow needle; it permits the mixing chamber to automatically lessen its volume as the mixed contents are removed to eliminate the need to introduce air into the chamber and thus reduce risk; it acts to automatically dislodge the safety shield once the contents of the chambers are combined. When mixing a solid and a liquid, the solid being in the mixing chamber, the use of the piston minimizes the amount of air or other gas in the mixing chamber.

The invention can be practiced in a manner which substantially prevents inadvertent mixing of the components. One way to do this is to mount a housing to the cylinder which partially defines the mixing chamber. A housing base is mounted to the receptacle partially defining the supplemental chamber. The housing and housing base are interconnected so that when the vial is in the inactivated condition, an axial force tending to telescope the housing and housing base together, which would result in collapsing the telescoping components, is prevented. Only when the housing and housing base are properly manipulated, such as by twisting the housing and housing base relative to one another so that a radially extending tab carried by the housing base enters an axially extending slot formed in the housing, can the components be telescoped together. This relative rotary motion can be normally restricted through the use of a safety seal or label adhered to both the housing and housing base. Only by breaking the safety seal or label would relative rotary motion between the two elements be possible.

Another safety feature which may be used instead of or in addition to the coupling of the housing and housing base, is a removable antiactivation cap used with the housing. The antiactivation cap and housing are sized so that they are at opposite ends of the vial and abut one another at their leading edges prior to causing the telescopic components to collapse into one another. Only after the antiactivation cap is removed can the components be telescoped into one another. The safety seal or label can also be used to prevent inadvertent or unauthorized removal of the antiactivation cap and plainly signal any such removal of the cap.

Other features and advantages of the invention will appear from the following description in which the preferred embodiments have been set forth in detail in conjunction with the accompanying drawings.

BRIEF DESCRIPTION OF THE DRAWINGS

FIG. 6 shows the device of FIG. 5 with the shield removed and a needle cannula of a syringe penetrating the piston to withdraw the mixed pharmaceutical.

FIG. 7 shows a cross-sectional view of an alternative embodiment of the invention having a diaphragm which includes a plug on a tether, the plug being dislodged from the diaphragm to open a channel allowing the two components to mix in the upper chamber.

FIG. 8 is a cross-sectional view of another alternative embodiment of the invention having a gasket connected to a plug by a perforated diaphragm which, when inserted in an aperture of the cylinder, separates the two chambers.

FIG. 9 is an engaged perspective, partial cross-sectional view of the gasket used in the embodiment illustrated in FIG. 8.

DESCRIPTION OF THE PREFERRED EMBODIMENT

Figure 1:
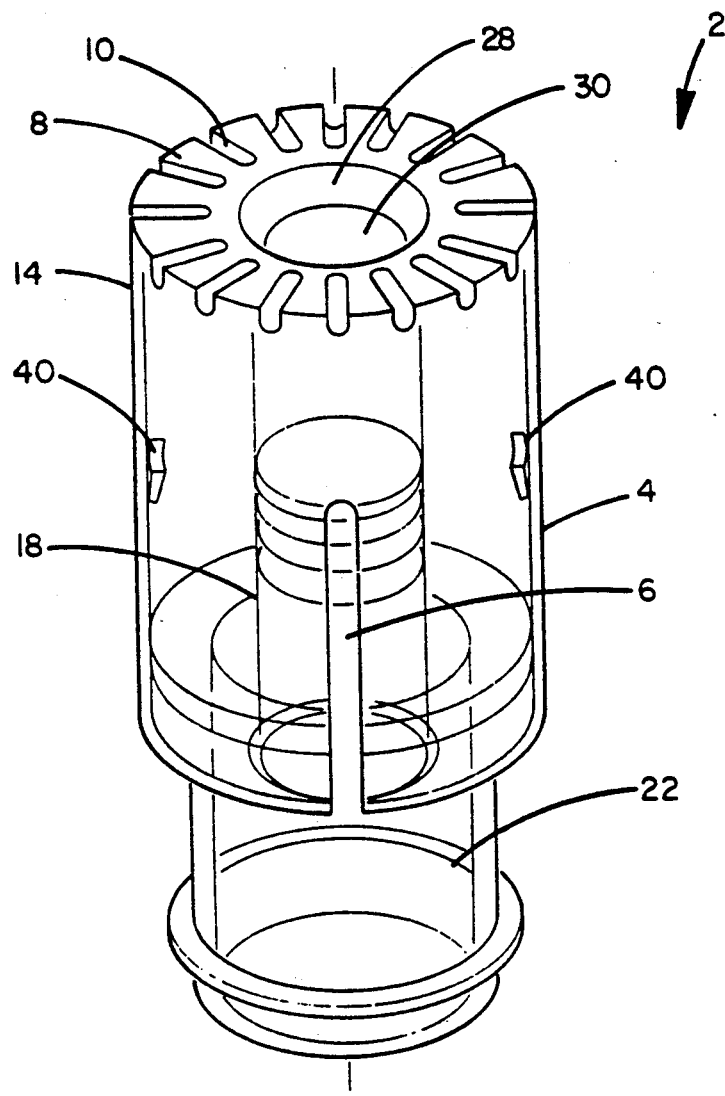
FIG. 1 is a perspective view of a preferred embodiment of the invention fabricated primarily from clear materials and showing the vial in the inactivated or premixed condition.
Figure 3:
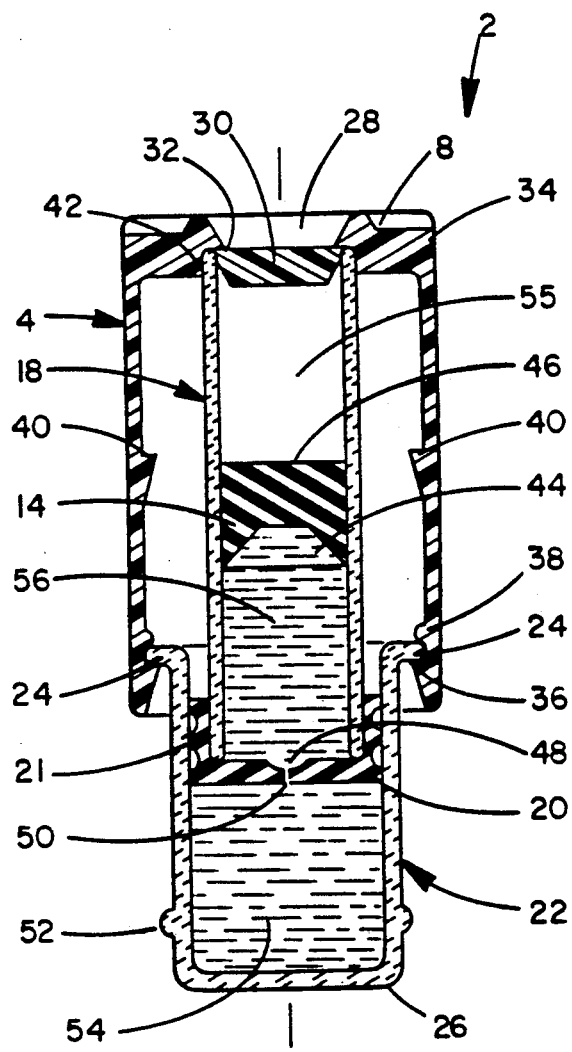
FIG. 3 is a cross-sectional view of the dual chamber vial in the inactivated condition of FIG. 1 showing a first and second chamber separated by a diaphragm.

Referring the reader to FIGS. 1 and 3, vial 2 includes a cylinder 18, piston 14, and a supplemental container or receptacle 22. Cylinder 18 and receptacle 22 are partially enclosed in housing 4. Housing 4, cylinder 18 and receptacle 22 are fabricated from transparent or translucent materials to allow the user to view the contents of vial 2. Cylinder 18 and receptacle 22 are preferably glass or a pharmaceutically compatible plastic; housing 4 is preferably made of polycarbonate.

Figure 13:
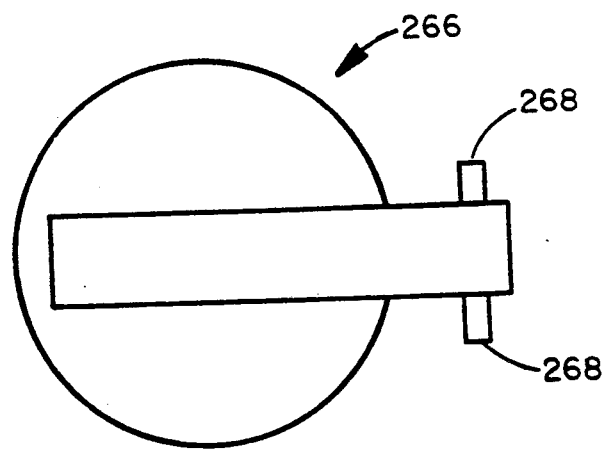
FIG. 13 is an enlarged end view of the safety shield of FIG. 10.
Figure 14:
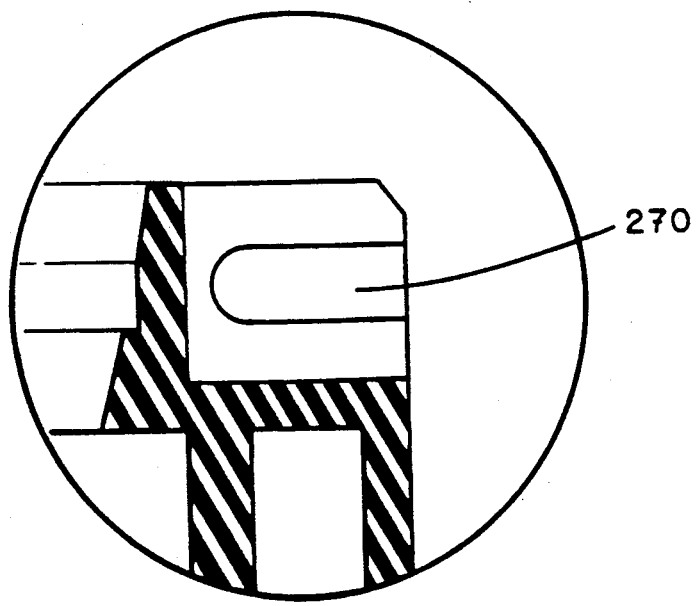
FIG. 14 is an enlarged cross-sectional view of the hinge portion of the housing taken along line 14—14 of FIG. 11A.

Housing 4 is cylindrical in shape and has a pair of expansion slots 6 located 180° apart. Upper surface 8 of housing 4 has a plurality of gripping slots lo to provide a non-slip surface for the user. A removable shield 30 is connected to housing 4 in a recessed housing aperture 28. Shield 30 is preferably a one-piece molded part with housing 4 and is connected to housing 4 by a continuous frangible connection 32. Alternatively, shield 30, as suggested in FIG. 13, could be friction fit or otherwise secured within the housing aperture 28. In either event, it is desired that shield 30 also keep the air space 55 above piston 14 sterile. Catch 40 is formed on the inner surface of housing 4. The function of catch 40 will be explained more fully below.

Figure 2:
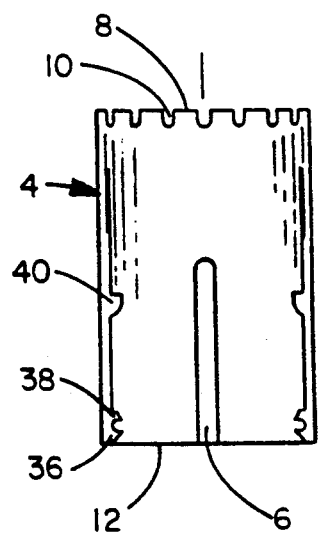
FIG. 2 is an exploded side view of the device shown in FIG. 1 illustrating the various component parts.
Figure 2:
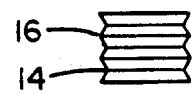
Figure 2:
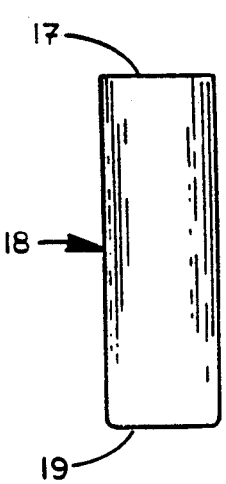
Figure 2:
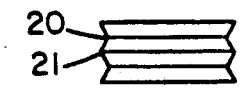
Figure 2:
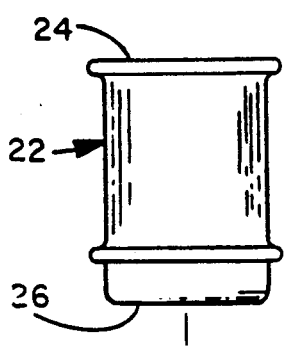

Referring now to FIG. 2, vial 2 is shown in an exploded view from the side showing the component parts. Housing 4 is open at its lower end 12. Cylinder 18 has a first end 17 and a second end 19. Piston 14 includes sealing ridges 16 sized to sealingly engage cylinder 18. Diaphragm 20 is made to be disposed about second end 19 of cylinder 18 and has sealing ridges 21 to create an air and liquid tight seal between outer surface of cylinder 18 and the inner surface of supplemental receptacle 22. Receptacle 22 is formed having a floor 26 and a rim 24. Rim 24 is formed to engage between a catch 36 and a protrusion 38 formed on housing 4 when in the premixed condition of FIGS. 1 and 3 or to engage with catch 40 on housing 4 when in the activated condition of FIG. 5.

Referring now to FIG. 3, showing vial 2 in the assembled and premixed condition, cylinder 18 is disposed between the upper surface 8 of housing 4 and receptacle 22. Housing 4 has a shoulder 34 and a seat 42 which is affixed to first end 17 of cylinder 18, such as by friction fit. Shield 30, frangibly connected to shoulder 34 at 32, covers the first end 17 of cylinder 18. Shield 30 is made of a rigid material which prohibits penetration by a needle cannula. As such, when shield 30 covers first end 17 of cylinder 18, a needle cannula cannot penetrate piston 14. Second end 19 of cylinder 18 is also precluded from penetration by a needle cannula in that it is enclosed by receptacle 22. Receptacle 22 is also made of a needle resistant material. In the preferred embodiment, housing 4 and receptacle 22 are transparent, but shield 30 is colored on it outer surface, preferably bright red, to indicate that access to cylinder 18 is restricted.

When piston 14 is disposed in cylinder 18 and diaphragm 20 is disposed on second end 19 of cylinder 18, an airtight and liquid-tight first chamber 56 is formed within cylinder 18. Diaphragm 20 seals between cylinder 18 and the inner surface of receptacle 22 such that when receptacle 22 is secured within housing 4 with rim 24 between catch 36 and protrusion 38, a second chamber 54 is formed between diaphragm 20 and floor 26 of receptacle 22. As shown in the cross section of FIG. 3, the result is a dual chamber vial 2 having a first chamber 56 housing a first component, and a second chamber 54 housing a second component when vial 2 is in the premixed condition. Airspace 55 is formed between shield 30 and a flat surface 46 of piston 14.

In the embodiment shown in FIG. 3, diaphragm 20 is formed having a cavity 48 forming a thin, reduced-strength membrane 50. The dimensions of membrane 50 are such that diaphragm 20 can be ruptured or torn at membrane 50 by sufficient fluid pressure as will be more fully described below.

Figure 4:
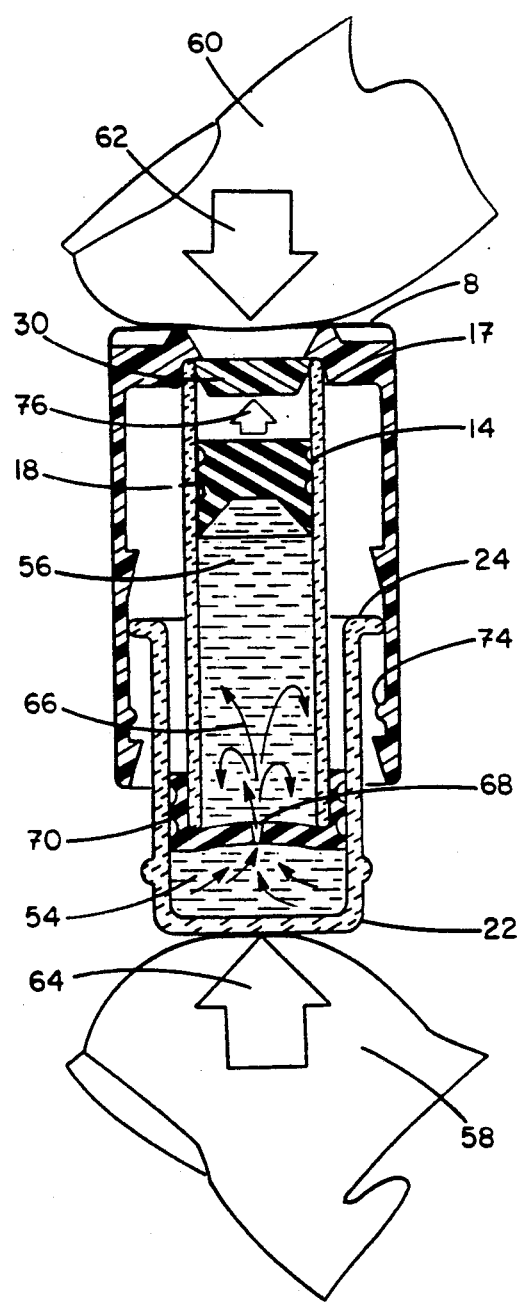
FIG. 4 shows the device in FIG. 3 being activated with the fluid pressure in the lower chamber tearing the diaphragm and causing turbulent mixing of the two components in the upper chamber with the piston travelling upwards as the upper chamber fills with both components.

Referring now to FIG. 4, vial 2 is shown being activated as it is compressed from the premixed condition. As previously stated, vial 2 in the premixed condition shown in FIG. 3, isolates components in the first chamber 56 from the components contained in second chamber 54. Separation of the two components may be desirable for shipping and storage. When it is necessary to combine the two components, the user grasps vial 2 by placing a finger against upper surface 8 of housing 4 and a second finger or thumb 58 against the outer surface of floor 26 of receptacle 22. The user then squeezes his or her two fingers 60, 58 together as indicated by arrows 62, 64. The resultant compression forces pressurizes the component located in second chamber 54 as receptacle 22 slides up within housing 4.

Initially, vial 2 is taken out of the premixed condition as rim 24 slides up and over protrusion 38. As rim 24 slides over protrusion 38, housing 4 is allowed to expand because of expansion slots 6. In the preferred embodiment, second chamber 54 is initially filled with a liquid component. As receptacle 22 slides up into housing 4 towards first end 17 of cylinder 18, fluid pressure in second chamber 54 increases. The increase in fluid pressure causes thin membrane 50 of diaphragm 20 to rupture, thereby providing a channel 68 between second chamber 54 and first chamber 56.

The user continues to assert compression force 62, 64 forcing the fluid contents of second chamber 54 through channel 68 and into first chamber 56 where the contents of second chamber 54 and first chamber 56 turbulently mix as indicated by arrows 66. As the components mix in first chamber 56, the fluid volume of chamber 56 increases proportionally. The increase in volume in chamber 56 drives piston 14 up in cylinder 18 towards shield 30 as indicated by arrow 76. Air in air space 55 escapes between the rim at first end 17 of cylinder 18 and seat 42; a grooved air path or a one-way valve (to ensure sterility) may be provided if desired. Only when the contents of second chamber 54 are completely exhausted into first chamber 56 is piston 14 driven against shield 30 into a post-mixed condition illustrated in FIG. 5.

Figure 5:
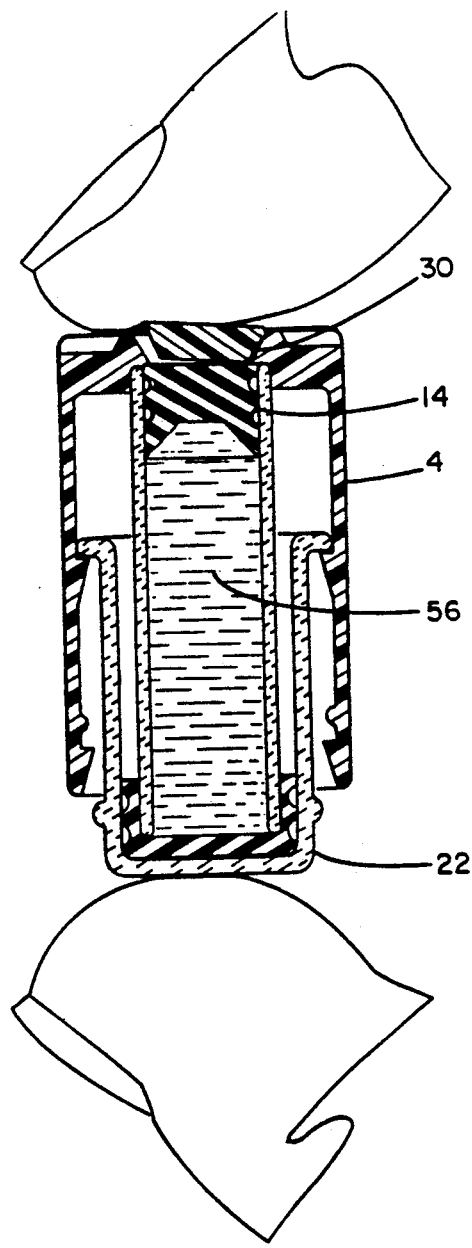
FIG. 5 shows the device illustrated in FIG. 4 in the fully activated position with the upper chamber filled with both mixed components and the shield dislodged from the safety position.
Figure 10:
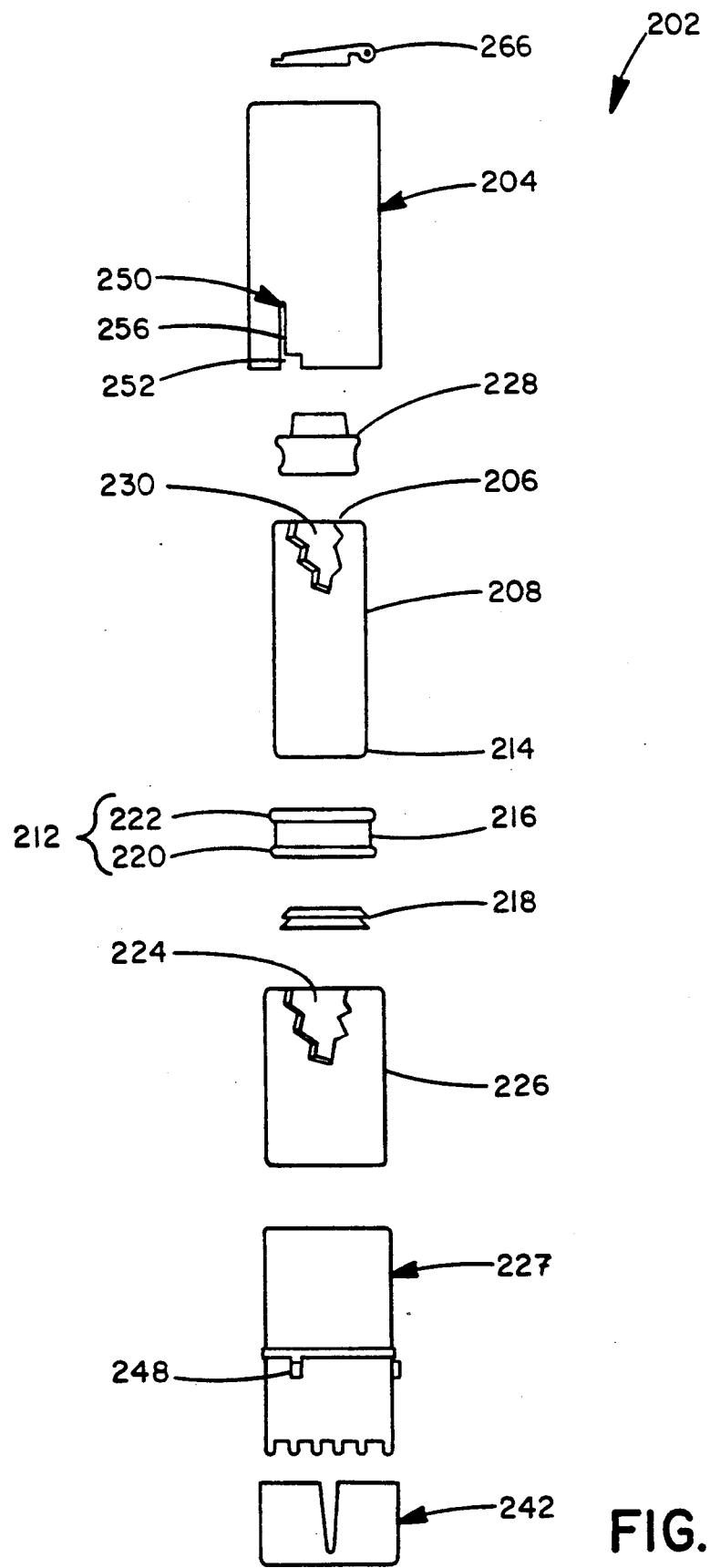
FIG. 10 is an exploded orthographic view of a further alternative embodiment of the vial of FIG. 1.

The post-mixed condition of vial 2, as shown in FIG. 5, is achieved when receptacle 22 is fully driven within housing 4 and the component parts of second chamber 54 and first chamber 56 have been turbulently mixed and combined within first chamber 56. When the increase in volume in first chamber 56 drives piston 14 into shield 30, shield 30 is dislodged from housing 4 by an audible snap. The audible snap is produced by breaking of the frangible connections between shield 30 and housing 4. Alternatively, when shield 30 is positioned within housing aperture 28 via a friction fit, as suggested in the embodiment of FIG. 13, audible pop as shield 30 is dislodged from its friction fit within housing aperture 28 may also be created. An aural indication is also created when rim 24 passes over catch 40. The user thus has an aural indication when shield 30 is dislodged from housing 4. This aural indicator, in conjunction with the freeing of shield 30, indicates to the user that the contents are fully mixed within the variable volume first chamber 56. Vial 2 is retained in the post-mixed condition by catch 40 retaining rim 24 of receptacle 22.

Once in the post-mixed condition, the shield 30 can be removed and a needle cannula 78 can be inserted through piston 14, which acts as a septum, as indicated in FIG. 6. Syringe 80 can now be used to draw out the contents of variable volume mixing region 56 located in vial 2. An important aspect of the invention is that as the contents of variable volume mixing region 56 is withdrawn from vial 2 through needle cannula 78, the fluid volume of variable volume region 56 decreases. As the volume decreases, the airtight and fluid-tight seals formed between piston 14 and cylinder 18, in combination with the seal formed by diaphragm 20 between receptacle 22 and cylinder 18, drives piston 14 down cylinder 18 towards second end 19 by hydraulic suction and prevents any ambient air from becoming entrained in variable volume region 56. This feature substantially prevents any inadvertent air bubbles from gathering within the pharmaceutical withdrawn from vial 2.

An alternative embodiment of the invention is shown in FIG. 7. In the alternative embodiment, diaphragm 82 has an opening 84 which is sealed by plug 86 in the premixed condition. Plug 86 may be connected to diaphragm 82 using tether 88. Plug 86 may also be a separate component as well. When vial 2a is activated from the premixed condition to the post-mixed condition, the increase in fluid pressure in second chamber 54 causes plug 86 to dislodge from opening 84 allowing the components to mix in first chamber 56 as previously described. This embodiment has the added feature that plug 86 can be used to additionally mix the components combined in first chamber 56 when the user forcibly shakes vial 2a causing plug 86 to work as an agitator.

A second alternative embodiment of the invention is illustrated in FIGS. 8 and 9. In the second alternative embodiment of the invention, cylinder 18b is formed having second end 19b with a small aperture 101. Gasket 92 seals between cylinder 18b and receptacle 22. Gasket 92 is more fully depicted in FIG. 9. Gasket 92 is formed having a plurality of holes 94 formed through a membrane 95 to which a stem 104 of plug 96 extends. Plug 96 is positionable in aperture 101 to seal and isolate first chamber 56 and second chamber 54 in the premixed position. When vial 2b is moved from the premixed position, fluid pressure in second chamber 54 causes plug 96 to be dislodged from aperture 101 forming a channel 110 between first chamber 56 and second chamber 54.

A further embodiment of the invention is shown in FIGS. 10-14. Vial 202 is similar to vial 2 and includes a housing 204 which mounts to the end 206 of a cylinder 208. This is achieved by positioning end 206 of cylinder 208 against a complementary mating surface 210 formed within housing 204. End 206 is preferably mounted to surface 210 using an adhesive or through a snug fit.

Figure 11A:
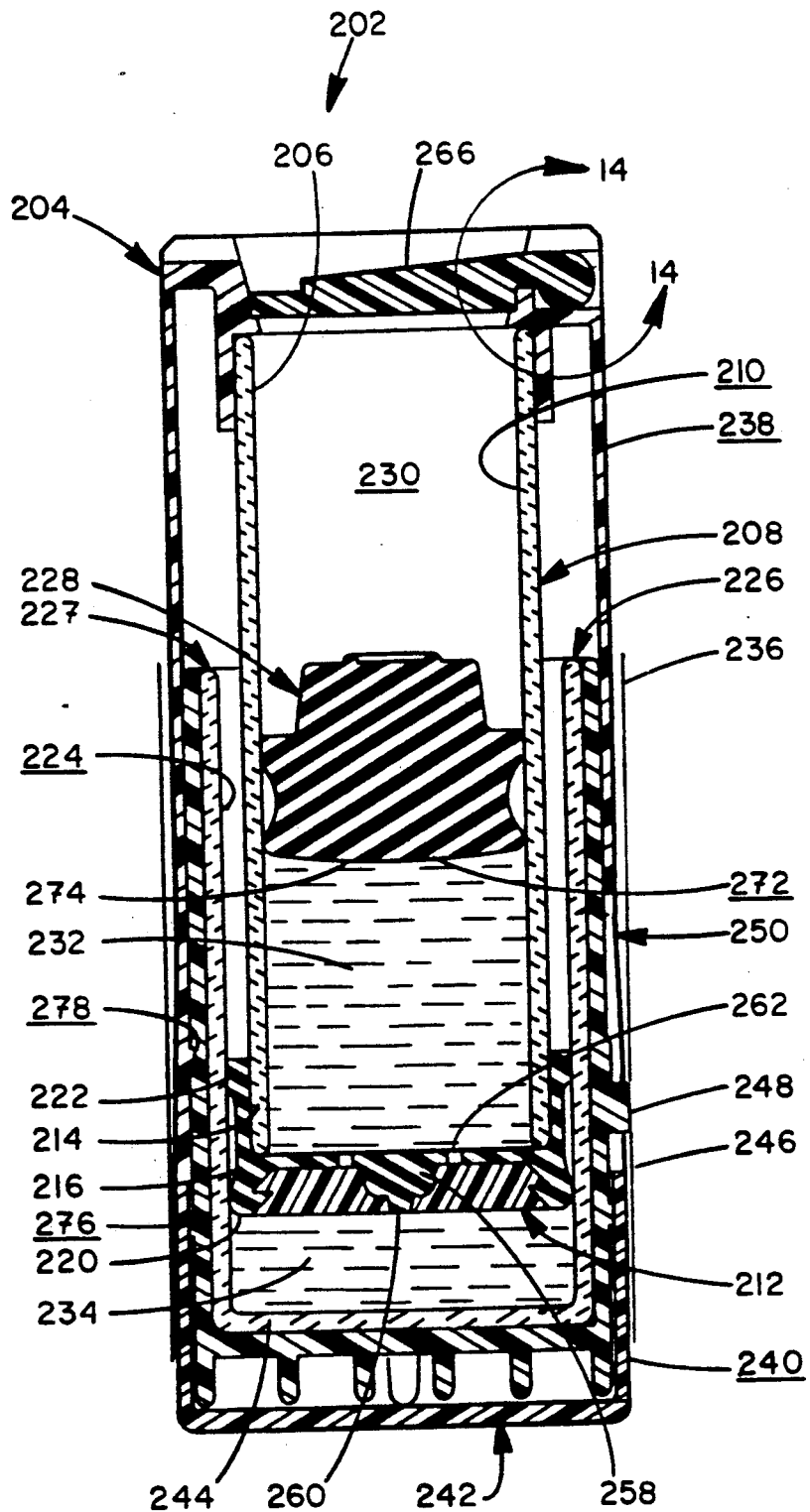
FIGS. 11A and 11B are side cross-sectional views of the vial of FIG. 10 in the inactivated, telescopically extended condition and the fully activated, telescopically collapsed condition.

Cylinder 208 includes a diaphragm assembly 212 mounted to a second end 214 of cylinder 208. Diaphragm assembly 212 includes an elastomeric sealing element 216 and a pharmaceutically inert insert 218, preferably PTFE, commonly sold as Teflon ®. Element 216 has external sealing ridges 220, 222 which engage the inner surface 224 of a cup-shaped receptacle 226. Receptacle 226 is preferably a cup-shaped glass container and is housed within a plastic protective housing 227. Protective housing 227, with receptacle 226 therein, is sized to fit closely but slidingly within housing 204 as shown in FIG. 11A.

Cylinder 208 includes an elastomeric piston 228 sized to move within the interior 230 of cylinder 208. Cylinder 208, piston 228 and diaphragm assembly 212 define a first, mixing chamber 232 which contains a first component. In the disclosed embodiment first, mixing chamber 232 houses a liquid; it could, however, house a dry or lyophilized component as well. A second, supplemental chamber 234 is defined by receptacle 226 and diaphragm assembly 212. Chamber 234 contains a flowable component, preferably liquid, which, upon activation of vial 202, flows into first, mixing chamber 232 so to mix with the first component for subsequent use.

Vial 202 has a tamper-evident seal 236 adhered to the outer surface 238 of housing 204 and the outer surface 240 of an antiactivation cap 242 mounted over the protruding end 244 of protective housing 227. Note that housing 204 and antiactivation cap 242 meet or abut at position 246. Thus, with cap 242 in place, an axial compression force on vial 202 would be resisted by housing 204 and cap 242 and not transferred to cylinder 208 and receptacle 226. After seal 236 is either broken or removed, cap 242 can be removed to permit access to protective housing 227.

Protective housing 227 has three equally spaced radially outwardly extending tabs 248 which engage three axially extending slots 250 formed in housing 204. Each slot 250 incudes an offset region 252 at an end adjacent position 246. With vial 202 in the inactivated condition of FIGS. 11A and 12A, radial tabs 248 are positioned in offset regions 252. To permit vial 202 to move from the inactivated condition of FIGS. 11A and 12A to the fully activated condition of FIGS. 11B and 12B, protective housing 227 is rotated in the direction of arrow 254 to move tab 248 from region 252 and into alignment with the main portion 256 of slot 250. The user then presses on the ends of vial 202 causing mushroom-shaped plug portion 258 of sealing element 216 to dislodge from inert insert 218 to permit fluid flow from second chamber 234, through a central opening 260 formed within insert 218, and through several holes 262 formed in element 216 and surrounding plug portion 258. The resulting flow is sufficiently turbulent to ensure appropriate mixing within first, mixing chamber 232.

Figure 12A:
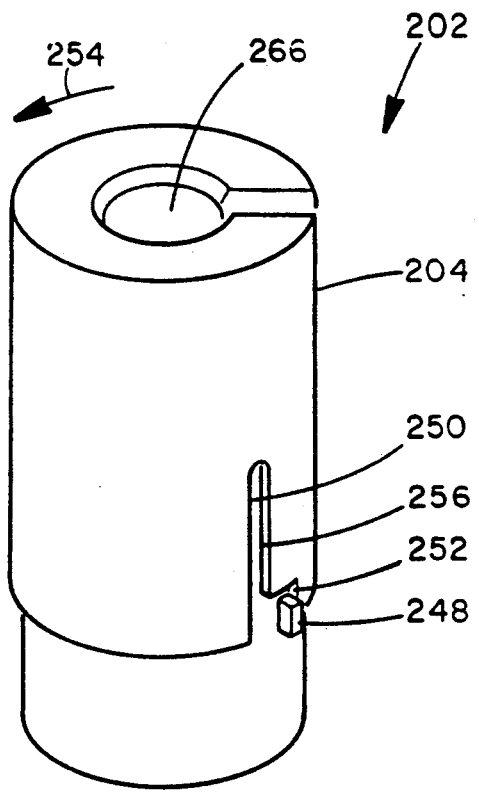
FIGS. 12A and 12B are external views of the vials of FIGS. 11A and 11B.
Figure 12B:
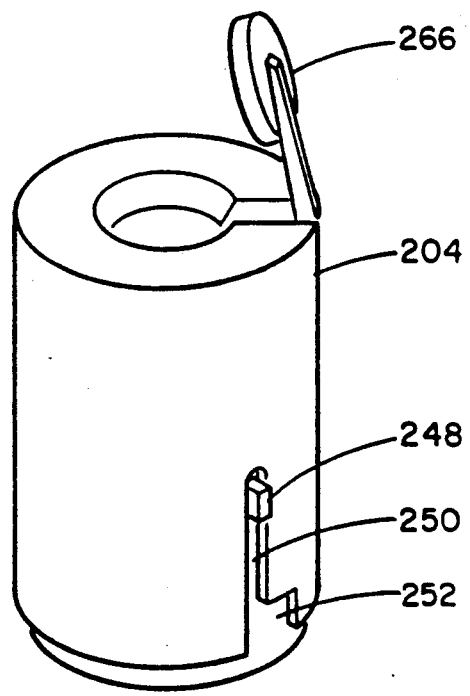

While this occurs, piston 228 moves within interior 230 towards a safety shield 266 which is positioned adjacent end 206 of cylinder 208. Safety shield 266, shown also in FIG. 13, includes pivot pegs 268 positioned within receptacles 270, see FIG. 14, formed in housing 204. As seen in FIGS. 12A and 12B, unlike safety shield 30 of vial 2, safety shield 266 remains attached to housing 204 when vial 202 is in its fully actuated condition. Although safety shield 266 is pivotally attached to housing 204, safety shield 266 could be an integral part of the housing with an integrally molded hinge and one or more frangible connections to keep the safety shield in position prior to activation.

Surface 272 has several slightly raised projections 274. This helps to prevent piston 228 from lying flush against elastomeric sealing element 216. Also, surface 272 is slightly concave so that as the user draws the mixed contents from chamber 232 (see FIG. 6), thus causing piston 228 to move towards sealing element 216, any liquid around the periphery of piston 228 during the final portions of such a movement will tend to be squeezed inwardly towards the center, thus being more accessible to the needle.

Figure 11B:
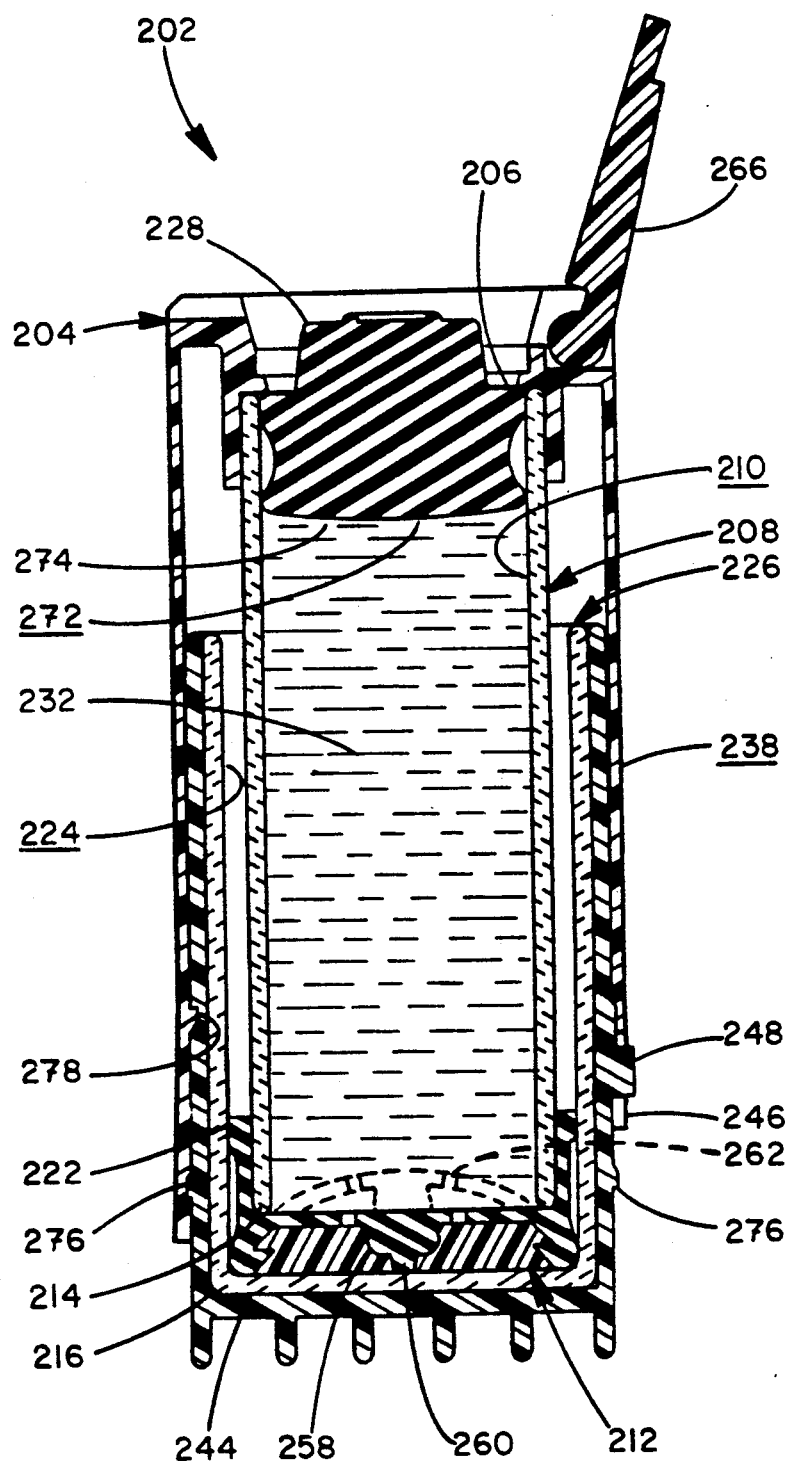

Once in the fully activated condition of FIGS. 11B and 12B, a rearwardly facing (that is, away from safety shield 266) abutment surface 276 formed by protective housing 227 engages a forwardly facing abutment surface 278 formed by housing 204 to substantially prevent separation of housing 204 and protective housing 227. This helps prevent the reuse of vial 202.

Other modifications and variations can be made to the disclosed embodiments without departing from the subject of the invention as defined in the following claims. For example, although the contents of the second chamber will generally always be a liquid, the contents of the first chamber, before mixing, can be a liquid, a slurry or a solid. The opening at the second end of the cylinder could be through the sidewall of the cylinder. The housings are quite useful but optional. If the housings are not used, the removable shield can be mounted directly within the interior of the cylinder adjacent its first end. This would, however, typically require some provision to permit air with an air space 55 to escape when moving from the premixed condition of FIG. 3 to the post-mixed condition of FIG. 5 while maintaining the interior of cylinder 18 sterile. This could be accomplished, for example, through the use of a one-way valve. The mixed pharmaceutical could be accessed in ways other than by piercing the elastomeric piston, such as by removing the piston or by removing a threaded plug formed within the piston.

What is claimed is:

1. A multi-chambered vial, comprising:

a compressible, air tight, telescoping vessel, said vessel having an open end and a closed end and comprising a first chamber and a second chamber, the first chamber and the second chamber coupled by an aperture filled with an air tight and fluid tight rupturable seal, the open end of the vessel made air tight by a displaceable piston disposed in the open end of said telescoping vessel and forming an air tight seal sealing the vessel from ambient air; and wherein when said telescoping vessel is compressed, pressure builds in the second chamber until the seal separating the first chamber and the second chamber is ruptured and the contents of the second chamber enter into the first chamber and turbulently mix with the contents of the first chamber, thereby increasing the volume in the first chamber by driving the piston towards the open end.

2. The vial of claim 1 further comprising:

a removable shield disposed over the open end of said vessel such that when said shield is positioned over said open end of said vessel said vessel is impenetrable to needle cannula; and wherein when the shield is dislodged from the vessel, a needle cannula can access the contents of the vessel through the piston.

3. The vial of claim 1 further comprising:

a needle cannula impenetrable shield positioned over said open end of said vessel to prevent needle cannula access to the piston, said shield being removable by the piston when the piston is driven towards the open end and against the shield until the shield is at least partially dislodged from the open end to permit needle cannula access to the piston.

4. A multi-chamber vial, comprising:

a housing having a removable shield, said housing and said shield both fabricated from material which prohibits penetration of a needle cannula;

a receptacle having an open end and a closed end, said open end having a rim formed about its periphery, said receptacle being slidably disposed relative to said housing, wherein said rim contacts said housing;

a cylinder disposed in said housing and having a first end and a second end, said first end coupled to said housing such that said shield forms a removable barrier over said first end, said second end extending away from said first end and having an aperture facing said receptacle;

a removable resilient member disposed in said aperture and forming a liquid tight seal in said aperture;

a piston disposed in said cylinder and forming a first chamber between said piston and said resilient member;

a gasket member disposed between said cylinder and said receptacle, said receptacle forming a second chamber sealed by said gasket member and said resilient member wherein the receptacle can be moved in said housing toward the cylinder causing fluid pressure to build in the second chamber until the resilient member is ruptured, thereby allowing the contents in the first chamber and second chamber to turbulently mix as the contents of the second chamber are forced through said aperture into the first chamber thereby increasing the fluid volume contained in the first chamber and driving the piston towards the shield, wherein when all the contents of the second chamber are forced into the first chamber said piston dislodges the shield from the open end of the cylinder to allow a needle cannula to access the contents of the first chamber through the piston.

5. A component mixing vial, for use with first and second components, the second component being a liquid component, comprising:

a mixing container having first and second ends, openings at the first and second ends and an elongate tube portion towards the first end;

a piston positioned within the elongate tube portion of the mixing container and movable from a premix position, away from the first end, to a post-mix position, towards the first end;

a seal towards the second open end of the mixing container, the first component being within a variable volume mixing region between the seal and the piston, the seal contacting the mixing container so as to sealably close the mixing container;

a supplemental container, containing the second component, the second open end being positioned within the supplemental container;

means for forcing the second component past the seal into the variable volume mixing region causing the first and second components to mix and forcing the piston towards the first end to the post-mix position; and means for accessing the mixed components within the variable volume region.

6. The vial of claim 5 wherein the accessing means includes a hollow needle pierceable portion of the piston so that the pierceable portion of the piston is pierceable by a hollow needle at the post-mix position to permit the mixed components within the variable volume region to be withdrawn through the hollow needle.

7. The vial of claim 6 further comprising a needle resistant shield aligned with the first end of the mixing container at a shield position for substantially preventing needle access to the piston when the piston is in the premix position, the shield being displaceable from the shield position by the piston when the piston is in the post-mix position to permit needle access to the piston.

8. The vial of claim 7 wherein the shield includes a plastic shield mounted over the open first end, the piston dislodging the plastic shield from the shield position when in the post-mix position.

9. The vial of claim 6, further comprising means for preventing needle access to the piston while the piston is in the premix position and for permitting needle access to the piston when the piston is in the post-mix position.

10. The vial of claim 5, wherein the mixing container is cylindrical.

11. The vial of claim 5, wherein the seal covers the second end.

12. The vial of claim 5, wherein the seal includes a diaphragm with a pressure sensitive weakened region.

13. The vial of claim 5 wherein the second component forcing means includes means for telescopically sliding the mixing container and the supplemental container towards one another.

14. The vial of claim 13, wherein the supplemental container slides over the second end of the mixing container.

15. The vial of claim 14, wherein the mixing container is cylindrical and the supplemental container is cup-shaped.

16. The vial of claim 13, wherein the second component forcing means includes a gasket sealingly positioned between the mixing container and the supplemental container.

17. A component mixing vial, for use with first and second components, the second component being a liquid component, comprising:
   a mixing container having first and second ends, openings at the first and second ends and an elongate tube portion towards the first end;
   a piston positioned within the elongate tube portion of the mixing container and movable from a premix position, away from the first end, to a post-mix position, towards the first end;
   a supplemental container telescopically mounted to the second end of the mixing container;
   a seal towards the second open end of the mixing container, the first component being within a variable volume mixing region within the container between the seal and the piston, the second component being within a variable volume storage region bounded at least in part by the supplemental container and the seal;
   wherein the seal contacts the mixing container so as to sealably close the mixing container;
   the seal including a normally sealed mixing path along which the second component can flow from the storage region to the mixing region as the mixing and supplemental containers are moved from a telescopically extended condition to a telescopically collapsed condition; and
   means for accessing the mixed components within the variable volume region.

18. The vial of claim 17 wherein the accessing means includes a hollow needle pierceable portion of the piston so the pierceable portion of the piston is pierceable by a hollow needle at the post-mix position to permit the mixed contents within the variable volume region to be withdrawn through the hollow needle.

19. The vial of claim 18 further comprising a needle resistant shield aligned with the first end of the mixing container at a shield position for substantially preventing needle access to the piston when the piston is in the premix position, the shield being displaceable from the shield position by the piston when the piston is in the post-mix position to permit needle access to the piston.

20. The vial of claim 19 wherein the shield is pivotally mounted to the mixing container.

21. The vial of claim 18 further comprising means for preventing the inadvertent movement of the containers to the telescopically collapsed condition.

22. The vial of claim 18 further comprising a housing mounted to the mixing container.

23. The vial of claim 22 further comprising a housing base mounted to the supplemental container.

24. The vial of claim 23 wherein the housing and the housing base include slot and extension means for helping to prevent inadvertent movement of the containers to the telescopically collapsed condition.

25. The vial of claim 23 further comprising antiactivation cap means, removably mountable to the supplemental container, for preventing movement of the containers to the telescopically collapsed condition by engagement with the housing.

26. The vial of claim 25 further comprising a tamper-evident seal associated with the antiactivation cap and the housing.

27. The vial of claim 26 wherein the seal is in the form of a label.

28. The vial of claim 25 further comprising a housing base mounted to the supplemental container and to which the antiactivation cap means is mounted.

* * * * *